US008217363B2

(12) United States Patent
Hatano et al.

(10) Patent No.: US 8,217,363 B2
(45) Date of Patent: Jul. 10, 2012

(54) SCANNING ELECTRON MICROSCOPE

(75) Inventors: Michio Hatano, Tokyo (JP); Takashi Ohshima, Saitama (JP); Mitsugu Sato, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 135 days.

(21) Appl. No.: 12/073,948

(22) Filed: Mar. 12, 2008

(65) Prior Publication Data

US 2008/0237465 A1 Oct. 2, 2008

(30) Foreign Application Priority Data

Mar. 26, 2007 (JP) ................................ 2007-080166

(51) Int. Cl.
*H01J 1/50* (2006.01)

(52) U.S. Cl. ................. 250/396 ML; 250/310; 250/311

(58) Field of Classification Search .................. 250/306, 250/307, 309–311, 396 R, 396 ML, 397–399, 250/492.1, 492.3

See application file for complete search history.

(56) References Cited

U.S. PATENT DOCUMENTS

| | | | | |
|---|---|---|---|---|
| 4,019,989 | A * | 4/1977 | Hazewindus et al. | 250/396 ML |
| 4,095,143 | A * | 6/1978 | Pridmore | 315/370 |
| 4,694,170 | A * | 9/1987 | Slodzian et al. | 850/9 |
| 4,785,176 | A * | 11/1988 | Frosien et al. | 250/396 ML |
| 6,329,826 | B1 * | 12/2001 | Shinada et al. | 324/751 |
| 6,590,210 | B1 * | 7/2003 | Essers | 850/9 |
| 6,852,982 | B1 * | 2/2005 | Bierhoff et al. | 250/396 ML |
| 7,105,816 | B2 * | 9/2006 | Kamiya et al. | 250/311 |

(Continued)

FOREIGN PATENT DOCUMENTS

JP 2001-256914 11/1988

(Continued)

OTHER PUBLICATIONS

"SEM_CROSSOVER", P. Finkel "Elec tron Microscopy", Feb. 20, 2007 <http://in.materials.drexel.edu/blogs/515_experimental_techniques/attachment/560.ashx>.*

(Continued)

*Primary Examiner* — Bernard E Souw

(74) *Attorney, Agent, or Firm* — Stites & Harbison, PLLC; Juan Carlos A. Marquez, Esq.

(57) ABSTRACT

A scanning electron microscope can discriminate secondary particles in a desired energy region by band-pass and detect the secondary particles with a high yield point. Even when a lens 23 is disposed on an electron source side of an objective lens 18, and a primary electron beam forms any optical system on the electron gun side of the lens, the lens operates the primary electron beam to be converged to a convergent point 24 that is a specific position. A detection ExB 16 that supplies a field that affects the locus of the secondary particles that are generated from a specimen 2 is disposed at the convergent point 24 of the primary electron beam so as to lead only the secondary particles in a specific energy range to a detection unit 13. Because a position to which the field that affects the locus of the secondary particles is supplied is the convergent point of the primary electron beam 19, it is possible to lead only the secondary particles of the desired energy to the detection unit without enlarging the aberration of the primary electron beam 19 and also to effectively conduct the band-pass discrimination of the energy. As a result, the signal electrons according to an observation object can be discriminated and detected.

5 Claims, 9 Drawing Sheets

U.S. PATENT DOCUMENTS

| | | | | |
|---|---|---|---|---|
| 7,141,791 | B2 * | 11/2006 | Masnaghetti et al. | 250/311 |
| 7,504,624 | B2 * | 3/2009 | Kawasaki et al. | 250/310 |
| 7,511,271 | B2 * | 3/2009 | Hatano et al. | 250/310 |
| 7,755,045 | B2 * | 7/2010 | Hatano et al. | 250/310 |
| 7,800,062 | B2 * | 9/2010 | Goldenshtein et al. | 250/310 |
| 7,825,377 | B2 * | 11/2010 | Kawasaki et al. | 250/306 |
| 2001/0010357 | A1 * | 8/2001 | Ose et al. | 250/311 |
| 2002/0185599 | A1 * | 12/2002 | Kimura et al. | 250/310 |
| 2004/0245465 | A1 | 12/2004 | Steigerwald et al. | |
| 2005/0012049 | A1 * | 1/2005 | Bierhoff et al. | 250/396 ML |
| 2006/0226360 | A1 | 10/2006 | Frosien | |
| 2008/0237465 | A1 * | 10/2008 | Hatano et al. | 250/311 |
| 2009/0008551 | A1 * | 1/2009 | Kawasaki et al. | 250/311 |
| 2009/0014649 | A1 * | 1/2009 | Nakasuji et al. | 250/310 |
| 2009/0101817 | A1 * | 4/2009 | Ohshima et al. | 250/310 |
| 2009/0230304 | A1 * | 9/2009 | Hatano et al. | 250/311 |
| 2010/0090109 | A1 * | 4/2010 | Hatano et al. | 250/310 |

FOREIGN PATENT DOCUMENTS

| | | |
|---|---|---|
| JP | 03-049142 | 7/1989 |
| JP | 2002-110079 | 9/2000 |
| JP | 2004-221089 | 1/2004 |
| JP | 2006-286207 | 3/2005 |
| JP | 2006-179504 | 3/2006 |
| JP | 2006-278329 | 3/2006 |

OTHER PUBLICATIONS

"def_cross", Free Online Encyclopedia, <http://encyclopedia2.thefreedictionary.com/crossover>.*

"crossover" at Dictionary.com, <http://www.elook.org/dictionary/crossover.html>.*

* cited by examiner

SCANNING ELECTRON MICROSCOPE

CLAIM OF PRIORITY

The present application claims priority from Japanese application JP 2007-080166 filed on Mar. 26, 2007, the content of which is hereby incorporated by reference into this application.

FIELD OF THE INVENTION

The present invention relates to a scanning electron microscope, and more particularly to a technique that effectively discriminates secondary particles that are generated from a specimen in energy in a band pass manner or in an emission cone angle manner with electron beams as a probe.

BACKGROUND OF THE INVENTION

There have been proposed a large number of detection systems that manipulate the orbits of secondary particles that are generated from a specimen, and discriminate the secondary particles by energy or emission cone angle (an angle defined between the optical axis of a primary electron beam and a direction of the emitted secondary particles) to detect the secondary particles.

For example, JP-A No. 2002-110079 discloses a scanning electron microscope that is capable of discriminating the secondary electrons lower in the energy and reflected electrons lower in the energy from each other, and discriminating the reflected electrons by the emission cone angle to detect the reflected electrons. The scanning electron microscope includes an ExB (orthogonal electromagnetic field generator) that deflects the electrons lower in the energy to a detection unit direction, and a first detection unit that detects the deflected electrons at an electron gun side of an objective lens. Also, at the electron gun side of the ExB, the scanning electron microscope includes a second detection unit that detects the secondary particles higher in the energy which have passed through the ExB.

The secondary electrons lower in the energy which have been emitted from the specimen are deflected to the detection unit direction by the ExB, and are detected. Also, parts of the reflected electrons higher in the energy, which are larger in the cone angle at the time of emission, are allowed to collide with the first electrode that is disposed between the objective lens and the ExB so as to be converted into signal electrons lower in the energy to detect the signal electrons as with the secondary electrons. On the other hand, parts of the higher energy reflected electrons, which are smaller in the cone angle at the time of emission, are converted into the signal electrons by the second electrode that is disposed at the electron gun side of the ExB to detect the signal electrons by the second detection unit.

The first detection unit detects both of the secondary electrons lower in the energy and the reflected electrons higher in the energy and larger in the cone angle. In this situation, a voltage is applied to the first electrode to change the polarity or intensity of the voltage. This makes it possible to change the mixture ratio of the two kinds of electrons which are detected by the first detection unit. For example, when only the secondary electrons are intended to be detected, a positive voltage is applied. As a result, the occurrence of the signal electrons is suppressed to detect only the secondary electrons. On the other hand, when only the reflected electrons are intended to be detected, a negative voltage is applied. As a result, a potential barrier is produced, and the secondary electrons are returned in the specimen direction and not detected. When an absolute value of the negative voltage is set to an appropriate value, the secondary electrons and the reflected electrons are mixed together at a constant mixture ratio so as to detect the secondary electrons.

Also, JP-A No. 2004-221089 discloses a scanning electron microscope which is capable of discriminating the secondary electrons with the low energy and the reflected electrons with the high energy from each other, and detecting the secondary electrons of high yield. The scanning electron microscope has an accelerator tube having a positive potential applied to the interior of the mirror body, and has two detection units in the interior of the accelerator tube.

The secondary particles that are generated from the specimen are pulled up to the interior of the mirror body by the accelerator tube, and directed toward the electron gun direction. In this situation, the locus is different according to the energy of the secondary particles, and the secondary electrons are focused on a location closer to a specimen table as the energy of the secondary electrons is lower.

The energy discrimination is detected as follows. The first detection unit that detects the secondary electrons lower in the energy is disposed on the optical axis where the secondary electrons are sufficiently dispersed after having being converged, to detect the second electrons. In this situation, because the reflected electrons higher in the energy pass through the center hole of the first detection unit, it is possible to detect only the secondary electrons.

The second detection unit that detects the reflected electrons higher in the energy is disposed on the optical axis where the reflected electrons are sufficiently dispersed after having been converged. An aperture is disposed on a location on which the reflected electrons are focused so as to enable the secondary electrons that have passed through the secondary electron detection unit to be blocked. The aperture travels on the optical axis, or the inner diameter of the aperture changes, thereby making it possible to optimize the yield point of the reflected electrons while the secondary electrons are appropriately blocked.

Further, JP-A No. Hei03-49142 discloses a method in which there is used an auxiliary lens for converging the secondary electrons to the electron gun side of an objective lens in order to enhance the detection efficiency of the secondary electrons in an SEM using a retarding method that enables high resolution observation at a low acceleration. In the method, only the secondary electrons that have been accelerated by the retarding voltage are converged at the electron gun side of the auxiliary lens by the auxiliary lens, and the detection unit is placed in a region where the secondary electrons are dispersed after having been converged, so as to detect only the secondary electrons. In order to reduce an influence of the auxiliary lens on the primary electron beams, the auxiliary lens is arranged at a position where the primary electron beam is converged.

SUMMARY OF THE INVENTION

The above conventional arts suffer from the following problems, respectively.

The ExB disclosed in JP-A No. 2002-110079 operates so as to deflect only the secondary electrons lower in the energy to a direction of the first detection unit. The reflected electrons higher in the energy pass through the ExB, and are then detected by the second detection unit that is disposed at the electron gun side. For that reason, an energy discrimination mechanism functions as high-pass discrimination with respect to the first detection unit, and functions as low-cut discrimination with respect to the second detection unit. That is, the band-pass detection is not assumed in the method.

In the principle, the ExB operates so as to deflect only a specific energy to the direction of the detection unit, thereby making it possible to conduct the band-pass discrimination detection. However, in the case where the energy of the secondary particles to be detected is large, the output of the ExB becomes large, the primary electron beams are largely affected by the output to enlarge the aberration.

Also, when the retarding voltage is applied to the specimen table, it is impossible to discriminate the secondary electrons by high pass for detection for the above reason because the secondary electrons have large energy.

In JP-A No. 2004-221089, it appears that the position of the aperture is changed on the optical axis to enable the band-pass discrimination of the reflected electrons with a desired energy to be detected. However, it is difficult to provide a movable aperture inside of the accelerator tube. Also, because the sensitive region of the detection unit is finite, when an attempt is made to detect the band-pass discrimination of the secondary particles relatively low in the energy, which is converged at a portion farther than the detection unit, because the secondary particles to be detected are largely emitted at the detection unit position, the yield position is deteriorated.

JP-A No. Hei03-49142 discloses the high-pass discrimination detection of the secondary electrons in using the retarding method, but does not assume the discrimination detection of the reflected electrons higher in the energy.

The present invention proposes a scanning electron microscope that is capable of discriminating secondary particles in a desired energy region by band pass and detecting the secondary particles with a high yield.

In order to achieve the above object, according to the present invention, there is provided a scanning electron microscope that scans a specimen with a primary electron beam which is emitted from an electron gun to obtain a scan image of the specimen, wherein there is disposed a crossover point formation unit that fixes one of a plurality of crossover points which are formed on an optical axis of the primary electron beam, which is closest to the specimen to a specific position, and secondary particles that are generated from the specimen by irradiation of the primary electron beam are detected by a detection unit. In this situation, a formation unit that forms an electric field/magnetic field which leads the secondary particles to the detection unit is disposed at the specific position where the crossover point is formed.

Also, according to the present invention, there is provided a scanning electron microscope that scans a specimen with a primary electron beam which is emitted from an electron gun to obtain a scan image of the specimen, comprising: a detection unit that detects secondary particles that are generated from the specimen by irradiation of a primary electron beam; a formation unit that forms an electric field/magnetic field which leads the secondary particles to the detection unit; and a crossover point formation unit for forming a crossover point of the primary electron beam at a specific position which is the operation center of the formation unit that forms the electric field/magnetic field.

In other words, according to the present invention, even if the crossover point formation unit that forms the crossover point of the primary electron beam to the specific position on the optical axis of the primary electron beam is disposed on the electron source side of the objective lens, and the primary electron beam forms any optical system on the electron source side of the crossover point formation unit, the crossover point formation unit operates so as to converge the primary electron beam to the specific position. Then, a field supply unit that is means for supplying a field that affects the locus of the secondary particles which are generated from the specimen is disposed on the crossover point of the primary electron beam, and only the second particles in a specific energy range is led to the detection unit. In the present specification, the "secondary particles" are a general name of the secondary electrons generated from the specimen by irradiation of the primary electron beam or the reflected electrons. Also, the "electric field/magnetic field" means any one of the electric field or the magnetic field, or both of the electric field and the magnetic field.

According to the present invention, because the position to which the field that affects the locus of the secondary particles is supplied is the crossover point of the primary electron beam, it is possible to lead only the secondary particles with a desired energy to the detection unit without enlarging the aberration of the primary electron beam. As a result, it is possible to effectively conduct the band-pass discrimination of the energy by control of the field supply unit, and it is possible to discriminate signal electrons according to the observation purpose and detect the discriminated signal electrons.

DETAILED DESCRIPTION OF THE PREFERRED EMBODIMENTS

Hereinafter, a description will be given in detail of diverse preferred embodiments of the present invention with reference to the accompanying drawings.

First Embodiment

Figure 1:
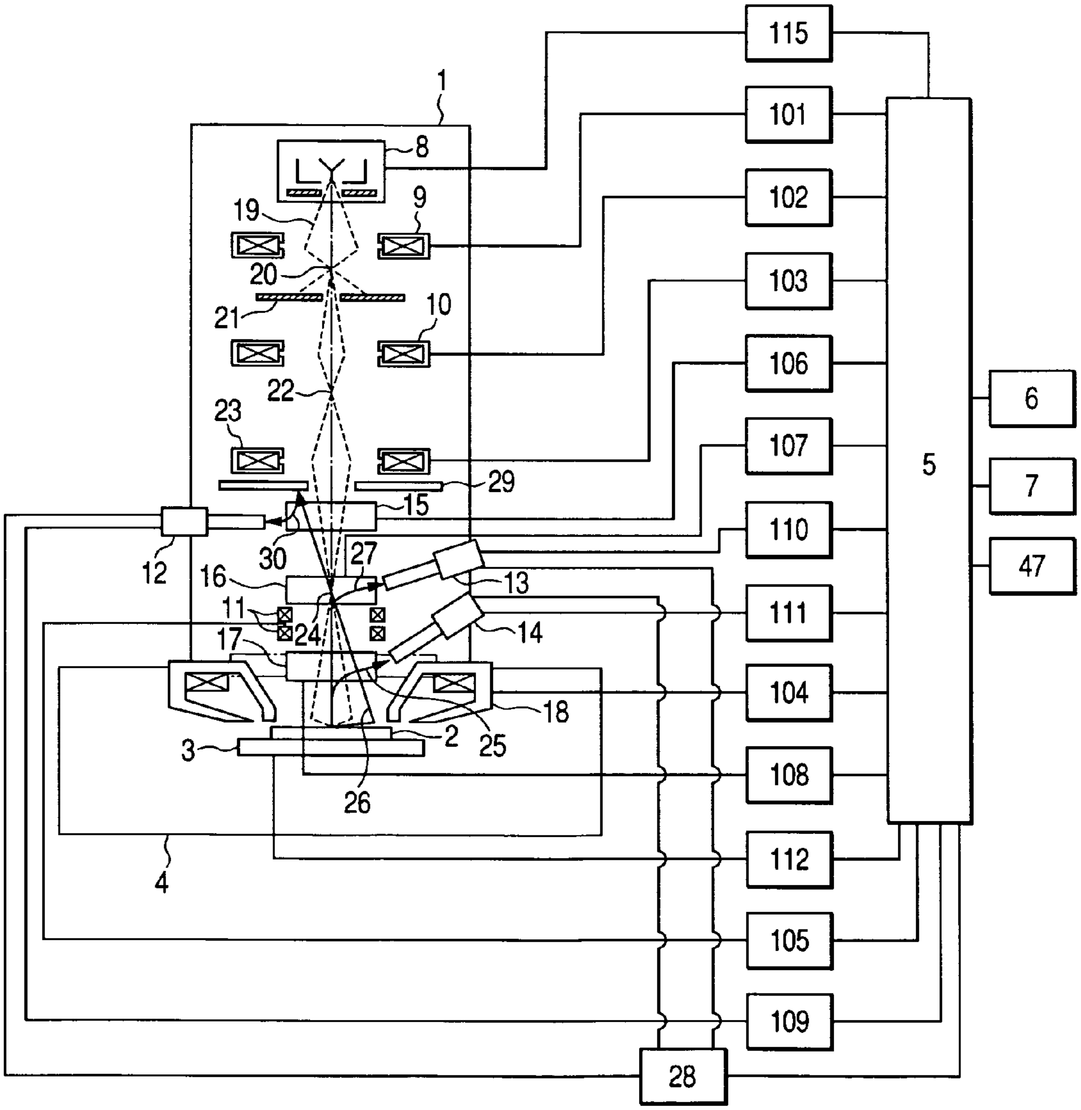
FIG. 1 is a diagram showing a scanning electron scanning microscope according to a first embodiment of the present invention.

FIG. 1 shows the entire structural diagram of a scanning electron microscope according to a first embodiment. The scanning electron microscope shown in FIG. 1 is roughly made up of an electron optical body tube 1 having a mechanism for irradiating an electron beam to a specimen, a sample chamber 4 that stores a stage 3 which holds a specimen 2 to be observed, diverse power supplies 101 to 115 for controlling the respective structural parts of the electron optical body tube 1 and the sample chamber 4, an information processing unit that conducts control processing, diverse image processing, or information processing related to a user interface, an image display system 6, and an image memory 7.

The electron optical body tube 1 includes an electron gun 8, a first condenser lens (C1 lens) 9, a second condenser lens (C2 lens) 10, a third condenser lens (C3 lens) 23, two scanning deflectors 11, a detection unit A12, a detection unit B13, a detection unit C14, a detection unit A ExB 15, a detection unit B ExB 16, a detection unit C ExB 17, and an objective lens 18. The objective lens 18 is a semi in-lens type objective lens that allows the specimen 2 which is disposed below a lower surface of the lens to be intentionally impregnated with an output magnetic field. The objective lens 18 may be disposed in the interior of the sample chamber 4. However, for convenience, the objective lens 18 will be described as a structural element belonging to the electron optical body tube 1.

A primary electron beam 19 that has been emitted from the electron gun 8 which is controlled by the electron gun power supply 115 is converged to a first crossover point 20 by means of the C1 lens 9 which is controlled by the C1 lens power supply 101, and thereafter passes through an objective lens aperture 21. In this case, an unnecessary region of the primary electron beam 19 is removed. The C1 lens 9 is so controlled as to control the position of the first crossover point 20 of the primary electron beam 19. The primary electron beam 19 that has passed through the objective lens aperture 21 is converged to a second crossover point 22 by means of the C2 lens 10 which is controlled by the C2 lens power supply 102. The C2 lens 10 is so controlled as to control the position of a second crossover point 22 of the primary electron beam 19. The primary electron beam 19 that has passed through the second crossover point 22 is converged to a third crossover point 24 by means of a C3 lens 23 that is controlled by the C3 lens power supply 103. The C3 lens 23 operates so as to form the third crossover point 24 at a specific position of the electron optical body tube 1 even if the optical system formed of the C1 lens 9 and the C2 lens 10 is any optical system. In other words, in this embodiment, the third crossover point 24 can be a crossover point that is formed at the specific position, and the C3 lens is a crossover point formation unit that converges the primary electron beam 19 to the specific position on the optical axis.

In this embodiment, the magnetic field lens is used as the C3 lens that functions as the crossover point formation unit to the specific position. However, the magnetic field lens is not always necessary, and an electrostatic lens or multiple multi-pole lenses can be used when the lens has the same converging operation. For example, when the multiple multi-pole lenses of the magnetic field or electric field superimposing type is used, a function of correcting a chromatic aberration or spherical aberration of the primary electron beam can be added except for the converging operation. As an example, four multi-pole lenses of the magnetic field or electric field superimposing type are proposed as disclosed in JP-A No. 2006-179504.

In this embodiment, the detection unit B ExB 16 is disposed in the vicinity of the third crossover point 24 so as to lead the secondary particles in the desired energy region to the detection unit. The detection unit B ExB 16 is controlled by the detection unit B ExB power supply 107. In other words, the detection unit B ExB 16 supplies a field that affects the locus of the secondary particles generated from the specimen, to thereby function as a field supply unit for leading the secondary particles in the desired energy region to the detection unit, and a formation unit that forms an electric field/magnetic field.

The primary electron beam 19 that has passed through the third crossover point 24 is converged on the specimen 2 by means of the objective lens 18 that is controlled by the objective lens power supply 104. The two scanning deflectors 11 that are controlled by the scanning deflector power supply 105 are disposed between the C3 lens 23 and the objective lens 18, and two-dimensionally scan the crossover point of the primary electron beam 19 on the specimen 2 according to a desired view field region/magnification ratio. The scanning deflector 11 supplies a vibration field for scanning the primary electron beam to the vicinity of the optical axis of the primary electron beam 19. The vibration field can be a vibration magnetic field or a vibration electric field. The arrangement position of the scanning deflector 11 is not specified to the above position, but, for example, can be arranged on the electron gun side of the C3 lens 23.

In this embodiment, the third convergent point 24 that is formed on the specific position on the optical axis is formed between the C3 lens 23 and the objective lens 18 as shown in FIG. 1.

An operator selects the energy of the primary electron beam 19, the intensity of the primary electron beam on the specimen 2, an incident angle/focal depth, or a view field/magnification ratio on the interface that is displayed in the image display system 6 before observation. The information processing unit 5 calls up the output values of the respective power supplies 115, 101, 102, 103, 105, and 104 of the electron gun, the C1 lens, the C2 lens, the C3 lens, the deflectors, and the objective lens from a data table that has been saved in an internal storage unit in advance, to operate the respective power supplies. The objective lens power supply 104 for the objective lens 18 can be so operated as to obtain a focused image while the operator is viewing the image.

Figure 10:
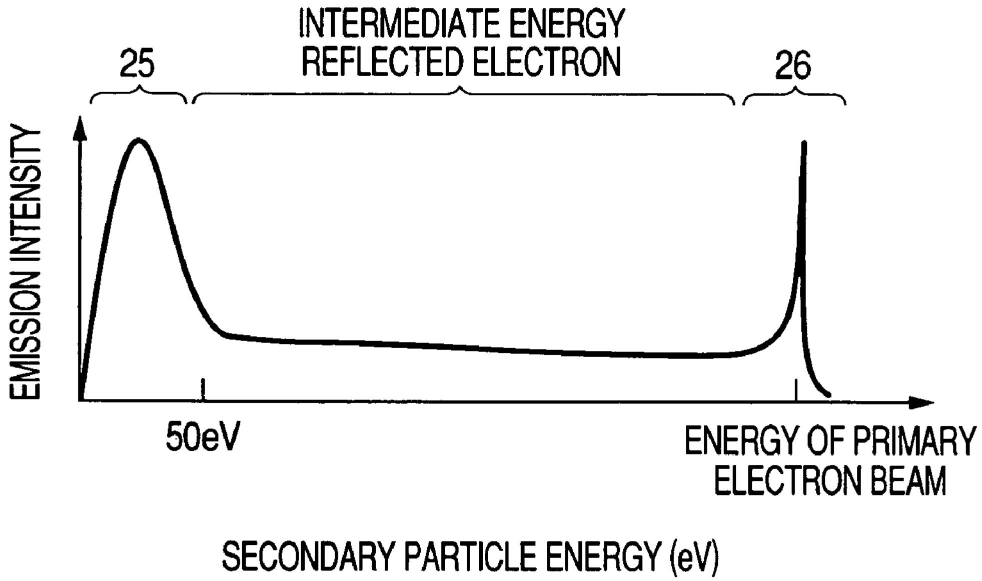
FIG. 10 is a diagram showing an energy dependency of the emission intensity of secondary particles from a specimen surface.

The irradiation of the primary electron beam 19 causes the secondary particles with diverse energies to be generated from the specimen. In the present specification, for convenience, when the specimen is of a ground potential, the electrons that are about 50 eV or lower in the energy of the secondary particles emitted from the specimen are called “secondary electrons 25”, the electrons having substantially the same energy as the energy of the primary electron beam immediately before being input to the specimen are called “high energy reflected electrons 26”, and the electrons having an intermediate energy between the secondary electrons and the high energy reflected electrons are called “intermediate energy reflected electrons”. FIG. 10 shows an example of an energy dependency of the emission intensity of the secondary particles from the specimen surface. In the figure, the axis of abscissa represents secondary particle energy (eV), and the axis of ordinate represents the emission intensity.

Hereinafter, a description will be given of an energy band-pass discrimination mechanism of the secondary particles which is a feature of this embodiment.

When the energy band-pass detection is conducted, the operator first selects the representative value of the energy of the secondary particles 27 to be detected on the interface that is displayed on the image display system 6. According to the selected value, the information processing unit 5 manipulates the detection unit B ExB power supply 107 to operate the detection unit B ExB 16 that is a field supply unit that is located at the specific position. In the case where the detection unit B ExB 16 is supplied, an electric field and a magnetic field which are orthogonal to each other are developed to satisfy the Vienna condition of the primary electron beam 19. Under the Vienna condition, the primary electron beam 19 passes without being affected by the deflecting operation, and only the secondary particles having the energy equal to or lower than the energy of the primary electron beam are deflected.

The degree of deflection to which the secondary particles are subjected depends on the energy of the secondary particles due to the detection unit B ExB 16 that is the field supply unit, and the secondary particles are more deflected as the energy of the secondary particles is lower. When the detection unit B ExB 16 operates so that the secondary particles 27 to be detected reach the center of the sensitive region of the detection unit B 13, the detected reflected electrons have the finite energy width around the representative value of the energy to be detected, thereby enabling the energy band-pass detection.

Figure 11:
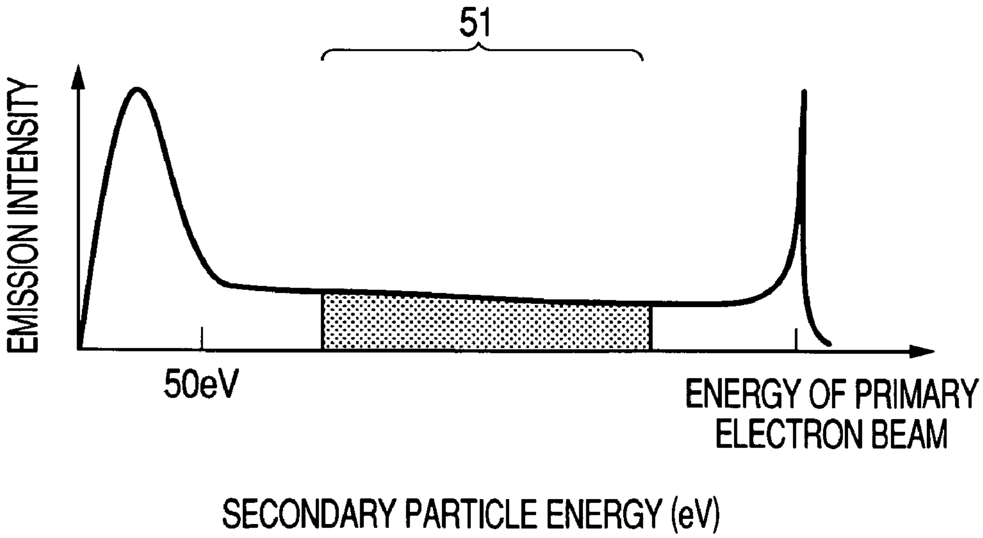
FIG. 11 is a diagram showing a select screen of an energy region of band-pass detection which is conducted on an interface.

FIG. 11 shows an example of a select screen in the energy region at the time of detecting the band-pass which is conducted on the interface of the image processing terminal 6. When the user selects the energy of the desired secondary particles through mouse operation or keyboard operation not shown, the information processing unit 5 extracts the output value of the necessary detection unit B ExB 16 from the parameter map that is, for example, stored in the storage unit, and also displays the energy region 51 of the secondary particles which can be detected in that case on the interface of the image processing terminal 6.

An Everhart Thornley (ET) type detection unit is used as the detection unit B 13. The ET type detection unit is made up of a scintillator whose surface is applied with a high voltage of about 10 kV, and a photo multiplier that converts the light emission of the scintillator into an electric signal. The voltage that is applied to the scintillator and the voltage that is applied to the photo multiplier are controlled by the photo multiplier power supply B 110. The detection unit B 13 is not limited to the ET type detection unit, but can be a semiconductor detection unit or a micro channel plate.

The signal output obtained by the detection unit B 13 is first taken in an image calculator 28. The image calculator 28 adjusts the gain of an analog signal, and converts the analog signal into a digital signal by means of an A/D converter. Thereafter, the image calculator 28 transfers the signal to the information processing unit 5. The information processing unit 5 generates a two-dimensional image from the signal that has been obtained in synchronism with the scanning of the primary electron beam 19, stores the generated image in the image memory 7, and simultaneously displays the image on the image display system 6 as a specimen image. As a result, the energy band-pass discrimination image of the intermediate energy reflected electrons is obtained.

According to this embodiment, the band-pass discrimination can be conducted with an arbitrary energy of the intermediate energy band. Also, even in the case where the energy of the secondary particles to be detected is high, and the intensity of the electric field and the magnetic field which are necessary for the deflecting operation is required to increase, because the supply location from the field supply unit is close to the third crossover point 24 which is formed at the specific position on the optical axis of the primary electron beam, the primary electron beam 19 is not largely affected by the increased intensity.

In order to effectively enhance the above advantage, it is necessary that the crossover point 24 is positioned to the operation center of the detection unit B ExB 16 as strictly as possible. For that reason, in the scanning electron microscope according to this embodiment, there is provided a positioning (focusing) unit of the crossover point 24 which is made up of the information processing unit 5.

The focusing operation can be conducted after the device starts up, or automatically every time the representative value of the energy of the secondary particles for detecting the energy of the primary electron beam or the band-pass is changed. In this case, the information processing unit 5 automatically starts the focusing operation at the respective timings. Alternatively, the operator starts the focusing operation on the interface of the image processing terminal 6 at an arbitrary timing.

Figure 12:
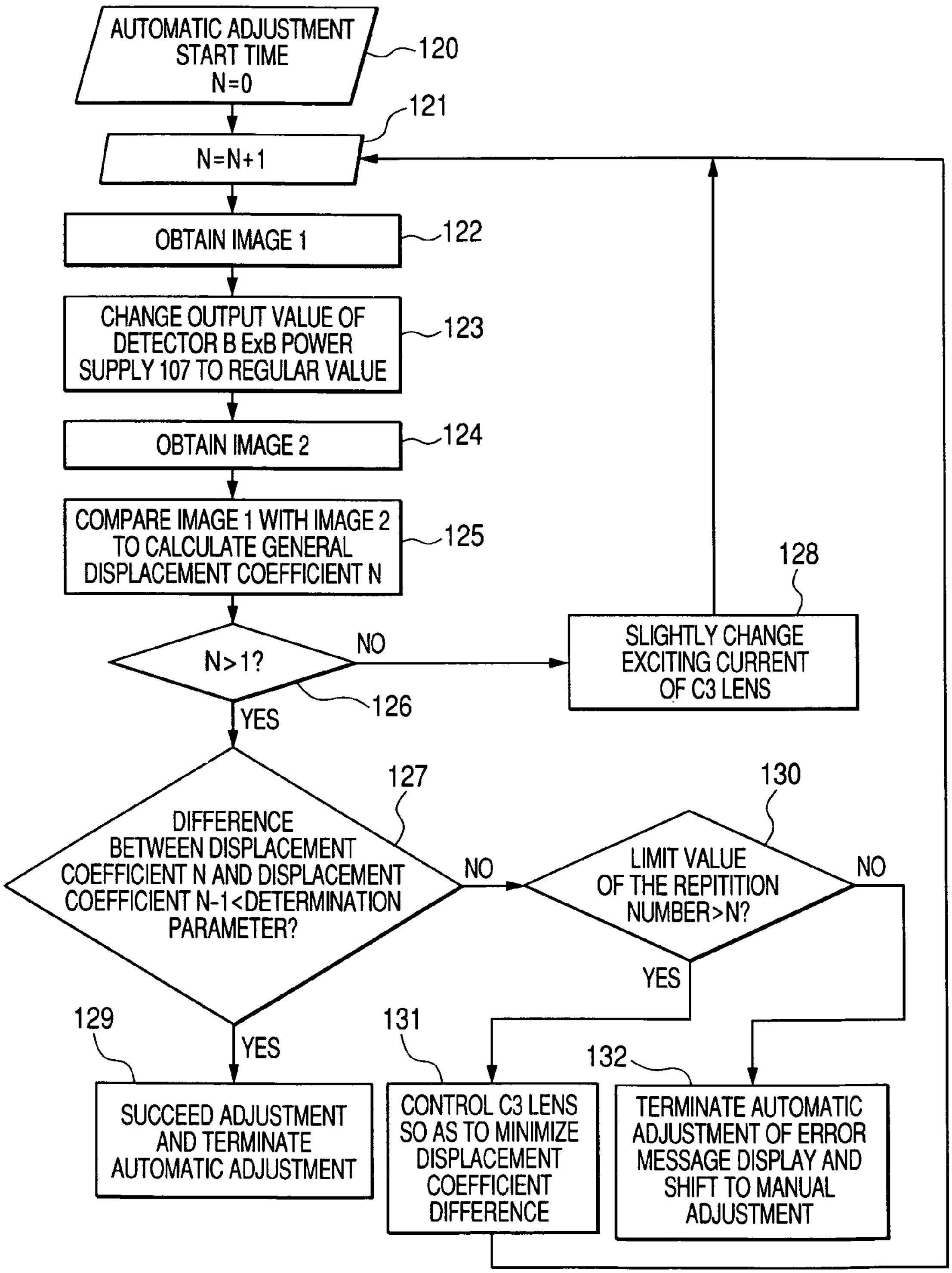
FIG. 12 is a flowchart showing the operation of automatically conducting focusing operation.

A flowchart of automatically conducting the focusing operation is shown in FIG. 12. The flowchart is a processing flow of program that is executed by a CPU (central processing unit) that constitutes the information processing unit 5.

First, an automatic adjustment starts (Step S120), the number of times is set to 1 in Step S121, and an image 1 of a structural object on the specimen is obtained in a state where the primary electron beam 19 is focused on the surface of the specimen 2 by the objective lens 18 (Step S122). Thereafter, the output value of the detection unit B ExB power supply 107 is changed to a regular value (Step S123), and a non-axisymmetric vibration electric field/vibration magnetic field is applied to obtain an image 2 (Step S124). In the information processing unit 5 of FIG. 1, those two images are compared with each other to calculate the coefficient of the positional displacement and the coefficient of the focal displacement on the specimen surface between the images (Step S125).

In the present specification, the coefficient of the positional displacement is a parameter representing the amount of displacement of the image of the structural object on the image surface between the image 1 and the image 2, and the coefficient of the focal displacement is, for example, a parameter that represents a difference in the sharpness of an edge portion of the structural object on the image. The coefficients of those displacements depend on the excitation current of the C3 lens 23. In general, in order to deal with the coefficient of the displacement in an integrated fashion, the general coefficients of the displacements including the information on those displacements are calculated (this value is called "general coefficient 1 of the displacement" for convenience). For example, the square sum of those displacements is used for the general coefficient of the displacement. Then, the information processing unit 5 slightly changes the exciting current of the C3 lens, 1 is added to the number of times, and two images are obtained similarly (Steps S126, S128, S121 to S125) to calculate the general coefficient of the displacement (this value is called "general coefficient 2 of the displacement).

The information processing unit 5 obtains a difference between the general coefficients 1 and 2 of the displacement, and compares the difference in the displacement coefficient with the value of the determination parameter. When the former is equal to or larger than the latter, the exciting current of the C3 lens such that the general coefficient of the displacement becomes minimum is calculated by the interior or the exterior to output the exciting current to the C3 lens power supply (Step S131). Also, likewise, the images 1 and 2 are obtained, and the general coefficient of the displacement (called "general coefficient 3 of the displacement") is calculated to obtain a difference between the general displacement coefficients 2 and 3. The same process is repeated until a difference in the general coefficient of the displacement becomes a value of the determination parameter or lower (Step S127). When the difference becomes lower than the determination parameter value, the adjustment is successful, and the automatic adjustment is terminated (Step S129). The number of repetition can be limited, and it is determined whether the number of repetition becomes equal to or higher than a limit value in a state where a difference in the displacement coefficient is not lower than the determination parameter, or not (Step S130), and when the number of repetition is not equal to or higher than the limit value, the control of the C3 lens is repeated so as to minimize the difference in the displacement coefficient when the number of repetition is not equal to or higher than the limit value (Step S131). When the number of repetition is equal to or higher than the limit value, the information processing unit 5 outputs an error message to the image processing terminal 6 to complete the automatic focusing (Step S132).

When the automatic focusing fails or when the user manually conducts focusing, the user instructs the information processing unit 5 to start a manual focusing procedure on the interface of the image processing terminal 6. In this situation, the information processing unit 5 applies the vibration current or vibration voltage to the detection unit B ExB power supply 107 to generate a non-axisymmetric vibration electric field/vibration magnetic field. The user controls the exciting current of the C3 lens on the interface or by a focusing knob 47 so as to minimize the image vibration and the periodic blur while viewing the image on the image processing terminal 6.

In this embodiment, there can be provided a detection unit system other than the above energy band-pass detection system B. Hereinafter, a description will be given of a higher energy reflected electron detection system A and a lower energy secondary electron detection system C, which are provided in the scanning electron microscope according to the first embodiment.

The energy band-pass detection system cannot detect the higher energy reflected electrons 26. This is because since the same locus as that of the primary electron beam 19 is drawn from the surface of the specimen 2 toward the electron gun 8, the higher energy reflected electrons 26 is converged at the crossover point 24 which is a specific position as with the primary electron beam 19, and is not affected by the deflecting operation of the detection unit B ExB 16.

In the higher energy reflected electron detection system, an axisymmetric electrode A29 is disposed at the electron gun side of the crossover point 24. When the higher energy reflected electrons 26 collide with the electrode A 29, the signal electrons 30 with a lower energy occurs. The signal electron 30 is deflected in a direction of the detection unit A 12 by means of the detection unit A ExB 15. The detection unit A ExB 15 is a Vienna filter that generates an electric field and a magnetic field which are orthogonal to each other so as to deflect only the signal electrons 30 in the direction of the detection unit A 12 without deflecting the primary electron beam to satisfy the Vienna condition of the primary electron beam. The detection unit A ExB 15 is controlled by the detection unit A ExB power supply 106.

The detection unit A 12 is an ET type detection unit as with the detection B 13, and a voltage that is applied to the scintillator and a voltage that is applied to the photo multiplier are controlled by the photo multiplier power supply A 109.

A method of detecting the higher energy reflected electrons 26 is not limited to a method using the detection unit A ExB 15. For example, the signal electrons can be detected by the ET type detection unit without using the ExB. In this situation, plural ET type detection units can be so disposed as to surround the optical axis. Also, a method of detecting the higher energy reflected electrons 26 is not limited to the method of converting the higher energy reflected electrons 26 into the lower energy signal electrons for detection. For example, a semiconductor or a micro channel plate can be disposed at a position of the electrode A 29 so as to directly detect the higher energy reflected electrons 26. No ExB is used in this case.

On the other hand, the secondary electrons 25 lower in the energy which are emitted from the specimen 2 are pulled up to the electron gun 8 side by means of the magnetic field of the objective lens 18.

In the secondary electron detection system, the secondary electrons 25 are deflected to the detection unit C 14 side by means of the detection unit C ExB 17 that is disposed at the electron gun side of the lower surface of the objective lens 18. The detection C ExB 17 generates an electric field and a magnetic field which are orthogonal to each other so as to deflect only the secondary electrons 25 in the direction of the detection unit C 14 without deflecting the primary electron beam to satisfy the Vienna condition of the primary electron beam. The detection unit C ExB 17 is controlled by the detection unit C ExB power supply 108.

The detection unit C 14 is the same ET type detection unit as the detection unit B 13, and a voltage that is applied to the scintillator and a voltage that is applied to the photo multiplier are controlled by the photo multiplier power supply C 111.

In this embodiment, there are used three deflectors consisting of the detection unit A ExB 15, the detection unit B ExB 16, and the detection unit C ExB 17. Among those ExB, the detection unit A ExB 15 and the detection unit C ExB 17 apply the electric field and the magnetic field to a portion that is not the crossover point of the primary electron beam 19, which causes the aberration to be created. The chromatic aberration that is generated by the detection unit A ExB 15 can be offset by appropriately setting the electric field and the magnetic field of the detection unit C ExB 17. A method of offsetting the chromatic aberration is conducted in the same manner as the method described in, for example, JP-A No. 2001-256914.

In this embodiment, there are provided the three detection systems as described above. Alternatively, it is possible to obtain the image resulting from mutually calculating the signals obtained by those three systems.

The signal outputs from the detection units A to C 12 to 14 are first taken in the image calculator 28. The image calculator 28 adjusts the gains of the analog signals of the three systems, and converts those adjusted analog signals into digital signals by the aid of an A/D converter, respectively. Thereafter, the image calculator 28 calculates the respective signals, or transfers the signals of the three systems to the information processing unit 5 without conducting the calculating operation.

In the case of conducting the image calculation, the operator selects how many images are obtained on the interface that is displayed on the image display system 6. Thereafter, the operator selects how to calculate the signal outputs of the detection units A to C 12 to 14 in each of those images. As one example, when it is assumed that the signal output of the detection unit A 12 is $\alpha$, the signal output of the detection unit B 13 is $\beta$, and the signal output of the detection unit C 14 is $\gamma$, the operator selects three images to be obtained, and selects a signal of $\alpha\times1+\beta\times0.5+\gamma\times0.1$ in the first image, a signal of $\alpha\times0+\beta\times1+\gamma\times(-1)$ in the second image, and a signal of $\alpha\times0+\beta\times0+\gamma\times1$ in the third image to be obtained. The information processing unit 5 stores the signals of the three systems which have been calculated according to the above calculation in the image memory 7, and displays the signals on the image display system 6.

In the case of conducting no calculating operation, the information processing unit 5 stores the signals of the three systems which are not calculated in the image memory 7, and displays a single or plural specimen images corresponding to the signals selected by the operator among the stored signals on the image display system 6.

In this embodiment, the three detection systems are provided, but the detection systems are not limited to three systems, and an arbitrary number of detection systems can be added as the occasion demands. Also, in this case, the number of inputs and the number of outputs in the calculation process of the above signals can be added according to the number of detection systems.

Also, in this embodiment, in order to conduct the high resolution observation under a condition where the energy of the primary electron beam on the specimen is low, a negative (retarding) voltage can be applied to the specimen. The energy of the primary electron beam 19 when passing through the objective lens 18 can be increased by application of the retarding voltage, thereby enabling the chromatic aberration to be reduced. In this case, the voltage that is applied to the specimen 2 on the stage is controlled by the retarding control power supply 112. Even in the case where the retarding voltage is applied, the convergence of the primary electron beam 19 on the specimen surface is adjusted by adjusting the lens intensity of the objective lens 18.

Because the secondary electrons during retarding have an energy corresponding to the retarding voltage, there is a case in which it is better to detect the secondary electrons by the detection unit B 13 by the aid of the energy band-pass detection system rather than the secondary electron detection system (detection unit C14). For example, in the case where the retarding voltage is X kV, the secondary electrons are accelerated by the retarding voltage, and pass through the third crossover point 24 of the primary electron beam 19 with an energy of about X keV. When a representative value of the energy to be detected in the band-pass detection system is set to X keV, the secondary electrons can be detected.

Second Embodiment

Figure 2:
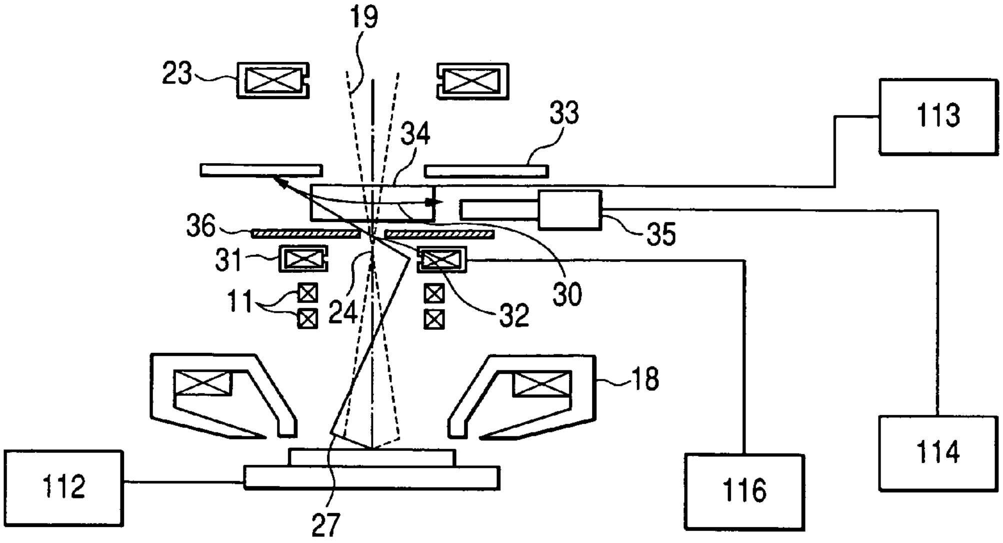
FIG. 2 is a diagram showing a scanning electron scanning microscope according to a second embodiment of the present invention.

FIG. 2 shows a part of the structure of a scanning electron microscope according to a second embodiment which is another embodiment of the present invention. The second embodiment is identical with the first embodiment shown in FIG. 1 except for the energy band-pass detection system.

In the second embodiment, an axisymmetric detection lens 31 that supplies a lens field at the third crossover point. The lens that functions as the field supply unit is not required to be a magnetic field lens, but can be an electrostatic lens or multiple multi-pole lenses when the same operation is conducted.

When the energy band-pass detection is conducted, the operator selects a representative value of the energy of the secondary particles 27 to be detected on the interface that is displayed on the image display system 6 as in the first embodiment. The information processing unit 5 manipulates the detection lens power supply 116 to operate the detection lens 31 so as to converge the secondary particles 7 to be detected to a crossover point 32 at the electron gun side of the crossover point 24. A display method on the interface, for example, follows the first embodiment.

The secondary particles 27 to be detected which have passed through the crossover point 32 are diffused, and collide with the axisymmetric electrode B 33 that is disposed on the electron gun side of the crossover point 32. When the secondary particles 27 collide with the electrode B 33, the signal electrons 30 with the lower energy are generated. The signal electrons 30 are deflected by the detection unit D ExB 34 in the direction of the detection unit D 35. The detection unit D ExB 34 forms a Vienna filter that generates an electric field and a magnetic field which are orthogonal to each other so as to deflect only the signal electrons 30 in the direction of the detection unit D 35 without deflecting the primary electron beam to satisfy the Vienna condition of the primary electron beam. The detection unit D ExB 34 is controlled by the detection unit D ExB power supply 113.

An ET type detection unit is used as the detection unit D 35. A voltage that is applied to the scintillator and a voltage that is applied to the photo multiplier are controlled by the photo multiplier power supply D 114.

The detection unit D 35 detects the signals derived from the secondary particles 27 that have collided with the electrode B 33. The reflected electrons having the energy lower than that of the secondary particles are converged on the specimen side of the crossover point 32. Also, the reflected electrons having the higher energy are converged on the electron gun side of the crossover point 32. For that reason, the reflected electrons that are detected by the detection unit D 35 have a finite energy width around the energy to be detected, thereby enabling the energy band-pass detection.

In order to control the width of the energy which conducts the band-pass detection, an aperture 36 is inserted between the C3 lens 23 and the electrode B 33. As a result, the aperture is disposed at the Crossover point 32 of the secondary particles 27 to be detected with the result that the energy of the secondary particles that are capable of passing in the direction of the detection unit is limited, thereby making it possible to more narrow the detection energy width. The aperture 36 can be fixed to the crossover point 32, or can be inserted from the exterior of the axis of the primary electron beam 19 so that the aperture 36 can be used when required. In the case where the aperture is of the insertion type, it is possible that the apertures of plural inner diameters are provided, and an insertion distance is so operated as to change the inner diameter of the aperture step by step. Further, the inserted aperture can be moved vertically in the direction of the optical axis.

The detecting method of the secondary particles 27 is not limited to the above method using the detection unit D ExB 34. For example, the secondary particles 27 can be detected directly by the ET type detection unit without using the ExB. In this situation, plural ET type detection units can be so employed as to surround the optical axis.

Also, the detecting method of the secondary particles 27 is not limited to a method of converting the secondary particles 27 into the low-energy signal electrons to detect the secondary particles 27. For example, a semiconductor or a micro channel plate can be disposed at a position of the electrode B 33 so as to directly detect the secondary particles 27. No ExB is used in this case.

A method of obtaining and displaying the image from the obtained signal is the same as that in the first embodiment.

According to the second embodiment, the band-pass discrimination can be conducted by the aid of an arbitrary energy in the intermediate energy band as in the first embodiment. Also, even when the energy of the secondary particles to be detected is high, and a field that is supplied by the detection lens 32 is required to increase for the purpose of convergence, because the supply location is at the third crossover point 24 of the primary electron beam, the primary electron beam 19 is not largely affected by the increased field.

In order to effectively enhance the above advantage, there is required a mechanism that always positions the crossover point 24 of the primary electron beam 19 to the supply point of the magnetic field of the detection lens 31 as strictly as possible, as in the first embodiment. For that reason, in this embodiment, there is provided a positioning unit of the crossover point 24 which is made up of the information processing unit as in the first embodiment. In the positioning, the operation conducted by the detection unit B ExB 16 that is a field supply portion is conducted by the detection lens 31 on the basis of the processing flow of one positioning example shown in FIG. 12 as in the first embodiment. In this case, because the detection lens 31 is axisymmetrically configured, when the output value of the detection lens power supply 116 which is applied to the detection lens 31 is changed to the regular value in Step S123 of FIG. 12, an axisymmetric vibration electric field/vibration magnetic field is generated.

Similarly, in the second embodiment, because the high resolution observation is conducted when the energy of the primary electron beam on the specimen is low, the retarding voltage can be applied to the specimen. In this case, the voltage that is applied to the specimen is controlled by the retarding control power supply 112. Even when the retarding voltage is applied, the convergence of the primary electron beam 19 on the specimen surface is adjusted by adjusting the lens intensity of the objective lens 18. The secondary electrons during retarding can be detected by the energy band-pass detection system as in the first embodiment.

In the second embodiment, there can be provided an electrode that applies a positive voltage (boosting voltage) to the vicinity of the objective lens 18 that is a magnetostatic lens to accelerate the primary electron beam 19. As a result, because the primary electron beam 19 can pass through the objective lens 18 in a state where the energy is high, a reduction in the chromatic aberration is realized. An embodiment in this case is shown in FIGS. 3 and 4.

Third Embodiment

Figure 3:
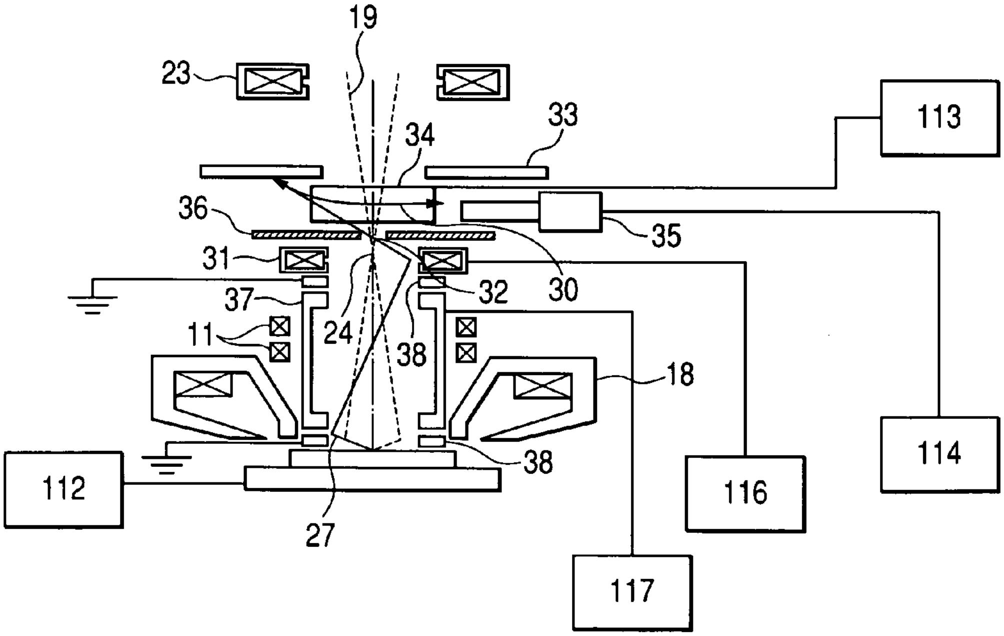
FIG. 3 is a diagram showing a scanning electron scanning microscope according to a third embodiment of the present invention.
Figure 4:
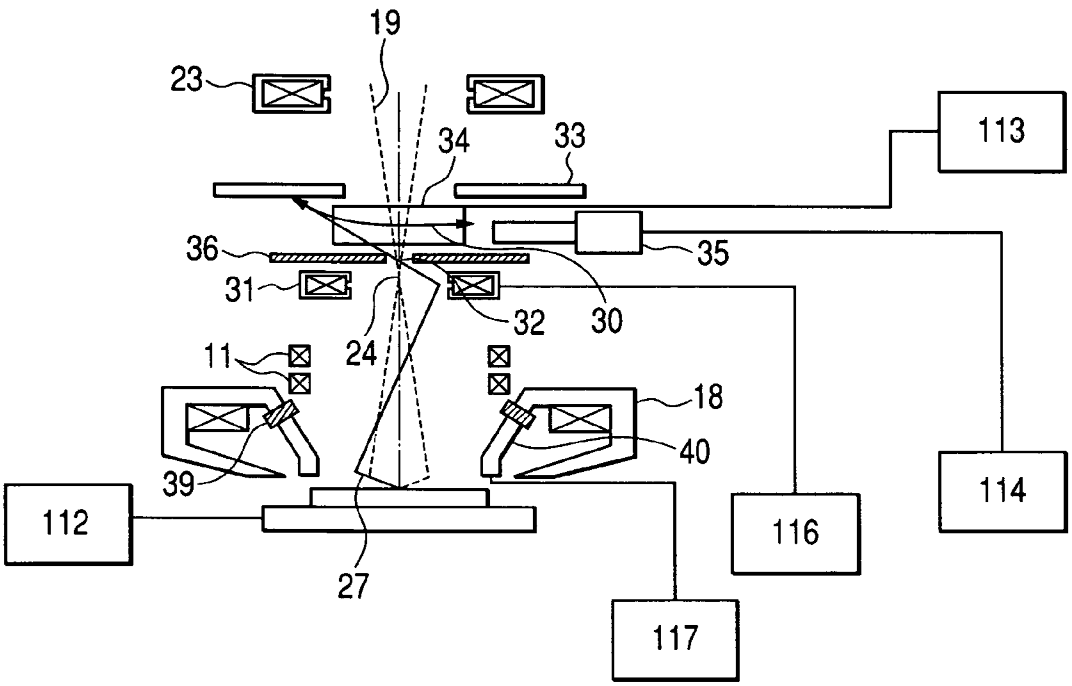
FIG. 4 is a diagram showing a scanning electron scanning microscope according to a fourth embodiment of the present invention.

FIG. 3 shows a third embodiment in which an einzel lens is superimposed on the objective lens 18 of the second embodiment.

An axisymmetric accelerating electrode 37 is disposed on the electron gun side of the lower surface of the objective lens 18. The boosting voltage that is applied to the accelerating electrode 37 is a high voltage whose absolute value is 1 kV to 10 kV, and is applied by the boosting power supply 117. In order to scan the primary electron beam 18, the scanning deflector 11 of the type that supplies the vibration magnetic field is disposed outside of the accelerating electrode 37. It is necessary that the accelerating electrode 37 is made of non-magnetic material so as not to shield the vibration magnetic field. Ground electrodes 38 that are axisymmetric and held to the ground potential are disposed above and below the accelerating electrode 37. Alternatively, the upper magnetic path of the objective lens 18 that is the ground potential can be used without providing a specific electrode to the ground electrode on the specimen side of the accelerating electrode 37.

With the above configuration, the einzel lens in which the energy of the primary electron beam does not change at the time of input and at the time of output is superimposed. Similarly, in this embodiment, the retarding voltage can be applied. The convergence of the primary electron beam 19 on the specimen surface is adjusted by adjusting the lens intensity of the objective lens 18 regardless of the presence or absence of application of the retarding voltage.

The secondary particles that have been generated from the specimen are accelerated by the voltage that is applied to the accelerating electrode 37 and the retarding voltage, and advance toward the electron gun direction. Then, the secondary particles are discriminated by the band-pass and detected from the detection unit D 35 as in the second embodiment. In this situation, the secondary electrons are also detected by the band-pass discrimination detection as in the case of applying the retarding voltage in the second embodiment.

Fourth Embodiment

FIG. 4 shows a fourth embodiment in which a positive voltage is applied to the upper magnetic path of the objective lens 18.

A part of the upper magnetic path of the objective lens 18 is a voltage supply magnetic path 40 that is insulated by an insulator 39. The voltage that is applied to the voltage supply magnetic path 40 is a high voltage whose absolute value is 1 kV to 10 kV, and is applied by the boosting power supply 117. With the configuration of the above electrode and the stage, in the case where the specimen is the ground potential, the einzel lens is superimposed, and in the case where the retarding voltage is applied, a decelerating type electrostatic lens in which the energy at the time of output is lower than the energy at the time of input is superimposed. The convergence of the primary electron beam 19 on the specimen surface is adjusted by adjusting the lens intensity of the objective lens 18 regardless of the presence or absence of application of the retarding voltage.

The secondary particles that have been generated from the specimen are accelerated by the voltage that is applied to the voltage supply magnetic path 40 and the retarding voltage, and advance toward the electron gun direction. Then, the secondary particles are discriminated by the band-pass and detected from the detection unit D 35 as in the second and third embodiments. In this situation, the secondary electrons are also detected by the band-pass discrimination detection as in the third embodiment.

In the above embodiment, the lenses that constitute the optical system that leads the primary electron beam 19 to the sample chamber in a desired optical system are made up of the C1 lens, the C2 lens, the C3 lens, and the semi in-lens type objective lens. When the band-pass detection system shown in the first embodiment and the second embodiment is provided, a scanning electron microscope with another configuration can be applied.

Fifth Embodiment

Figure 5:
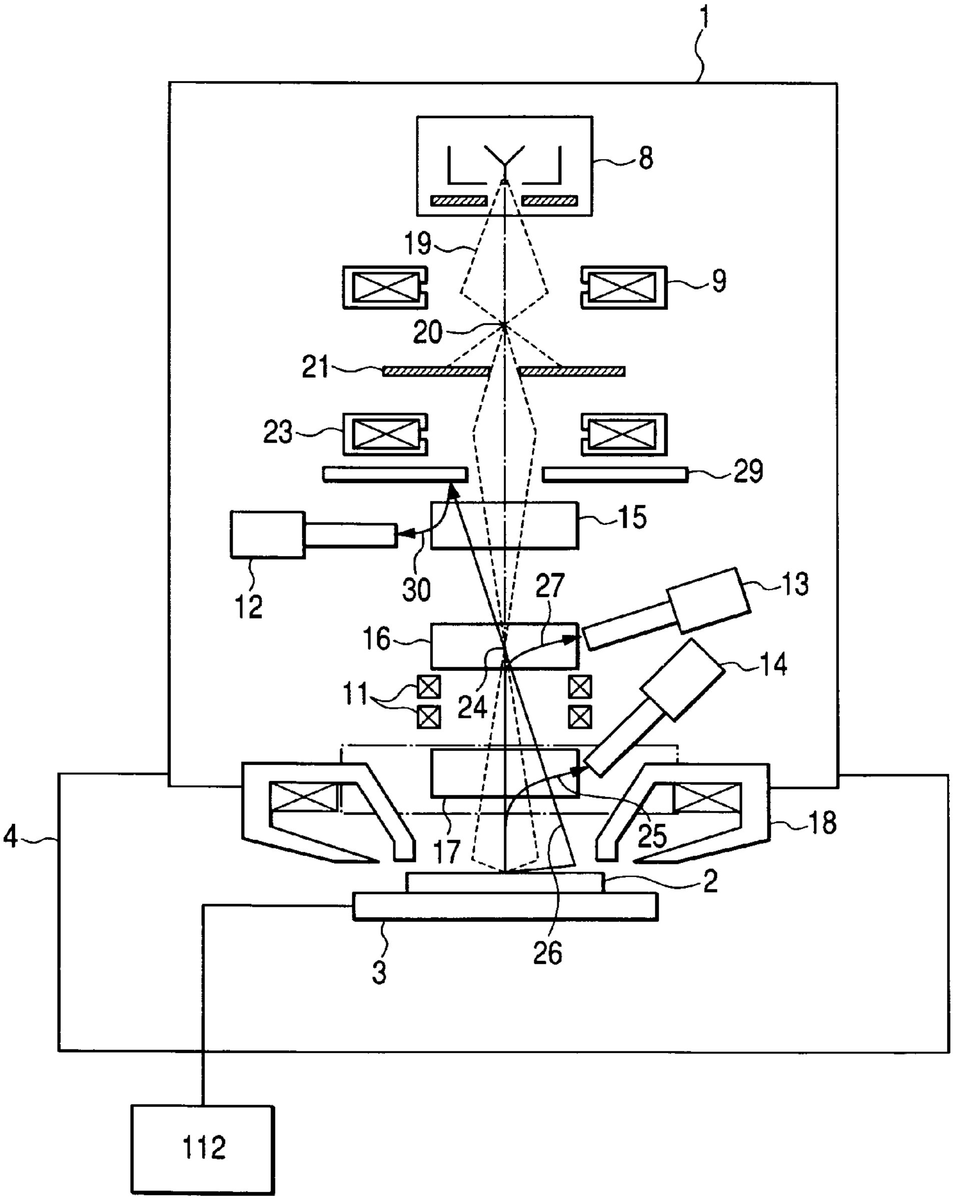
FIG. 5 is a diagram showing a scanning electron scanning microscope according to a fifth embodiment of the present invention.

A fifth embodiment shown in FIG. 5 is a scanning electron microscope of the type having no C2 lens in the first embodiment. This type can shorten the body tube and is inexpensive because one lens is reduced.

Also, the objective lens of the scanning electron microscope is not limited to the semi in-lens type magnetic field objective lens shown in the first to fifth embodiments. Hereinafter, a description will be given of embodiments of variations of the objective lens.

Sixth Embodiment

Figure 6:
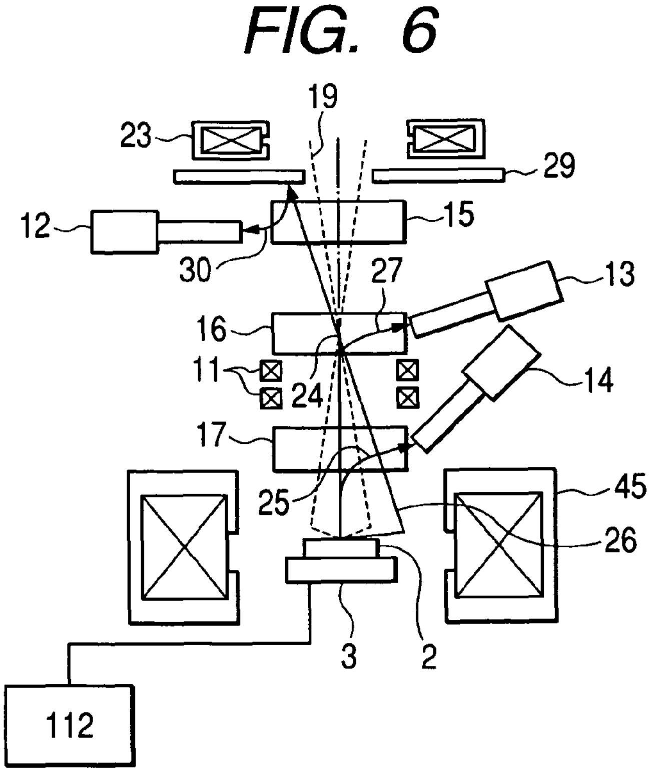
FIG. 6 is a diagram showing a scanning electron scanning microscope according to a sixth embodiment of the present invention.

A sixth embodiment shown in FIG. 6 is a scanning electron microscope having an objective lens (in-lens type objective lens) 45 of the type in which the specimen is disposed in the interior of the objective lens. According to this type, the specimen 2 can be placed in the magnetic field with a higher intensity, and the aberration can be effectively reduced, as compared with the objective lens in the first to fifth embodiments. However, there is disadvantageous in that the observation of the magnetic specimen whose sizes are limited is difficult. The detection of the secondary particles is conducted in the same manner as that in the scanning electron microscope of the first embodiment.

Seventh Embodiment

Figure 7:
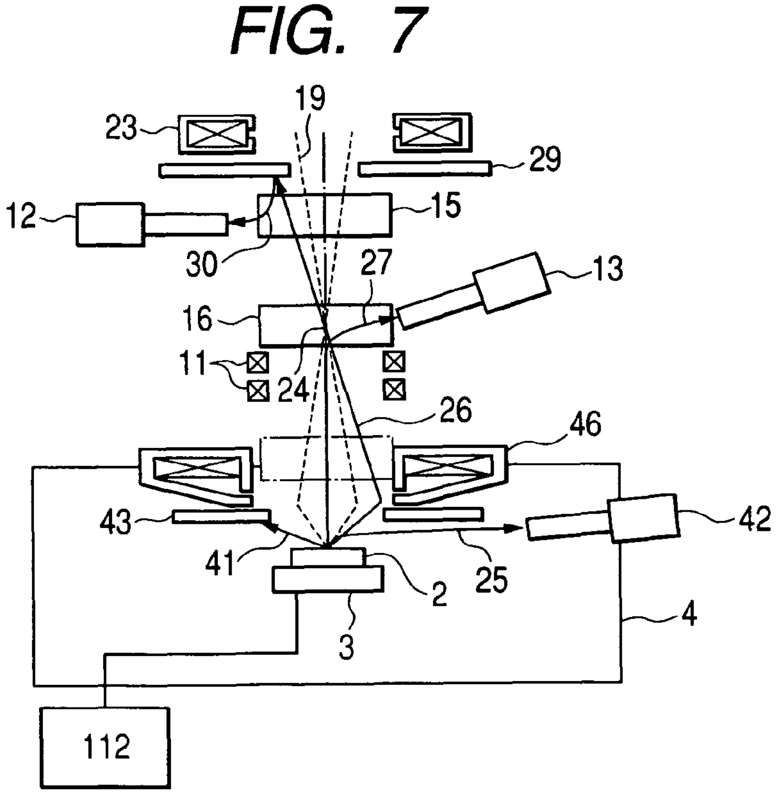
FIG. 7 is a diagram showing a scanning electron scanning microscope according to a seventh embodiment of the present invention.

A seventh embodiment shown in FIG. 7 is a scanning electron microscope having an objective lens (out-lens type objective lens) 46 of the type in which the magnetic field of the objective lens does not penetrate into the specimen 2. In this type, observation is enabled even when the specimen is made of a magnetic material. The detection of the secondary particles is conducted in the same manner as that of the scanning electron microscope in the first embodiment. However, when the retarding voltage is not applied to the stage, because the specimen is not in the magnetic field, the secondary electrons do not generally pass through the objective lens. In order to detect the secondary electrons, a detection unit E 42 is disposed within the sample chamber. The detection unit E 42 is an ET type detection unit, and the secondary electrons 25 are pulled by a positive voltage of about 10 kV which has been applied to the surface so as to be accelerated for detection.

Also, large cone angle reflected electrons 41 that do not pass through the objective lens are detected by a detection unit F 43 that is disposed on the specimen side of the lower surface of the objective lens. The detection unit F 43 is formed of a semiconductor detection unit or a micro channel plate. The same detection unit as the detection unit F 43 can be disposed in the first to fifth embodiments.

Eighth Embodiment

Figure 8:
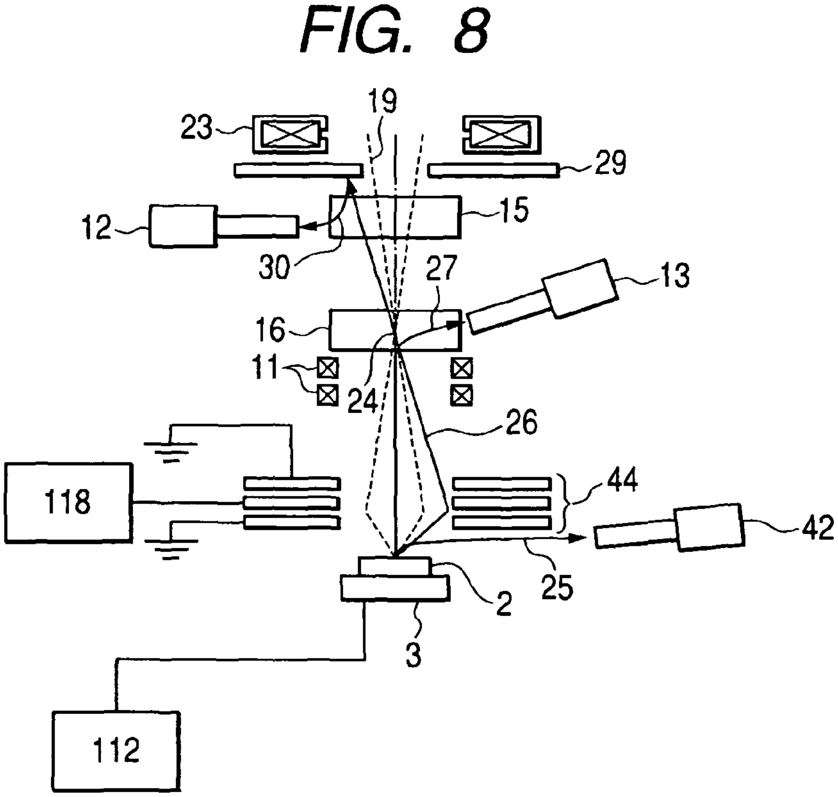
FIG. 8 is a diagram showing a scanning electron scanning microscope according to an eighth embodiment of the present invention.

An eighth embodiment shown in FIG. 8 is a scanning electron microscope of the type that uses an electrostatic lens 44 as the objective lens. The electrostatic lens 44 is an einzel lens having a configuration an axisymmetric electrode that applies the voltage is interposed between axisymmetric electrodes that are held to the ground potential. The electrostatic lens 44 is controlled by the electrostatic lens control power supply 118.

The band-pass discrimination detection systems in the fifth to eighth embodiments are described on the basis of the configuration of the first embodiment. However, it is needless to say that those band-pass discrimination detection systems can be configured by the band-bass discrimination detection system of the second embodiment.

Ninth Embodiment

Finally, a description will be given of an embodiment in which the detection lens is used, and the second particles different in information can be discriminated and detected at the same time in the band-pass detection, as in the second embodiment.

The locus of the secondary particles which are affected by the excitation of the detection lens 31 depends on not only the energy but also the emitted cone angle (an angle defined between the optical axis of the primary electron beam and the direction of the secondary particles). Plural detection units are arranged by using the above fact, thereby making it possible to detect and detect plural secondary particles different in the information at the same time.

Figure 9:
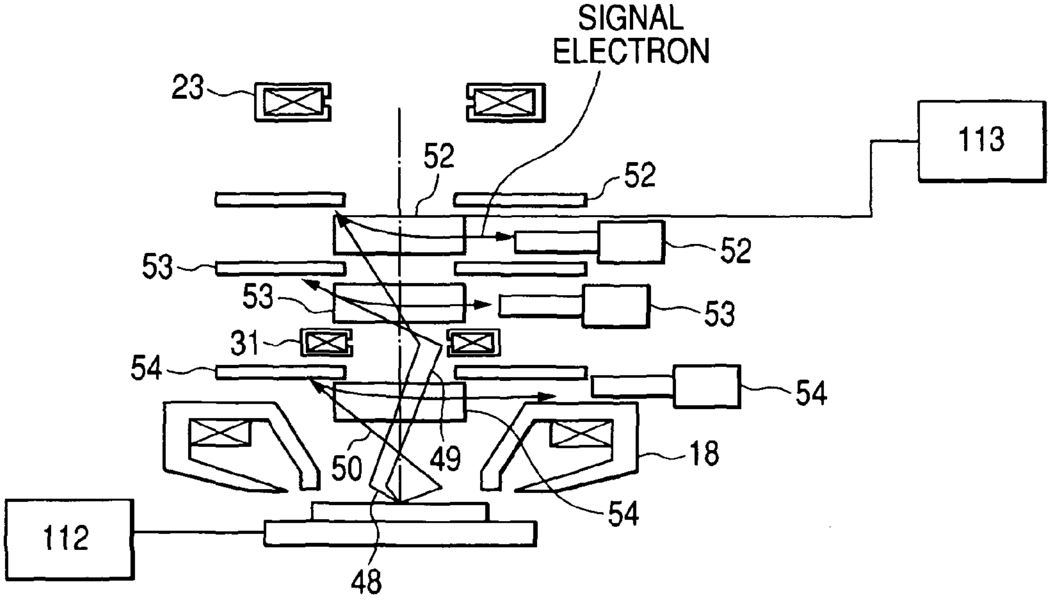
FIG. 9 is a diagram showing a scanning electron scanning microscope according to a ninth embodiment of the present invention.

For example, in the structure of FIG. 9, there are provided three sets of detection units of the type having the combination of the electrode 33, the ExB 34, and the ET detection unit 35 described in the second embodiment. When the exciting condition of the detection lens 31 is set to a given value, as shown in FIG. 9, a detection unit 52 closest to the electron gun side can discriminate and detect the reflected electrons small in the emission cone angle (high-energy small-cone angle reflected electrons 48) among the high energy reflected electrons, a detection unit 53 at an intermediate position can discriminate and detect the electrons 49 having the intermediate energy to be detected, and a detection unit 54 closest to the specimen side can discriminate and detect the reflected electrons large in the emission cone angle (high-energy large-cone angle reflected electrons 50) among the high energy reflected electrons at the same time, respectively.

Figure 13:
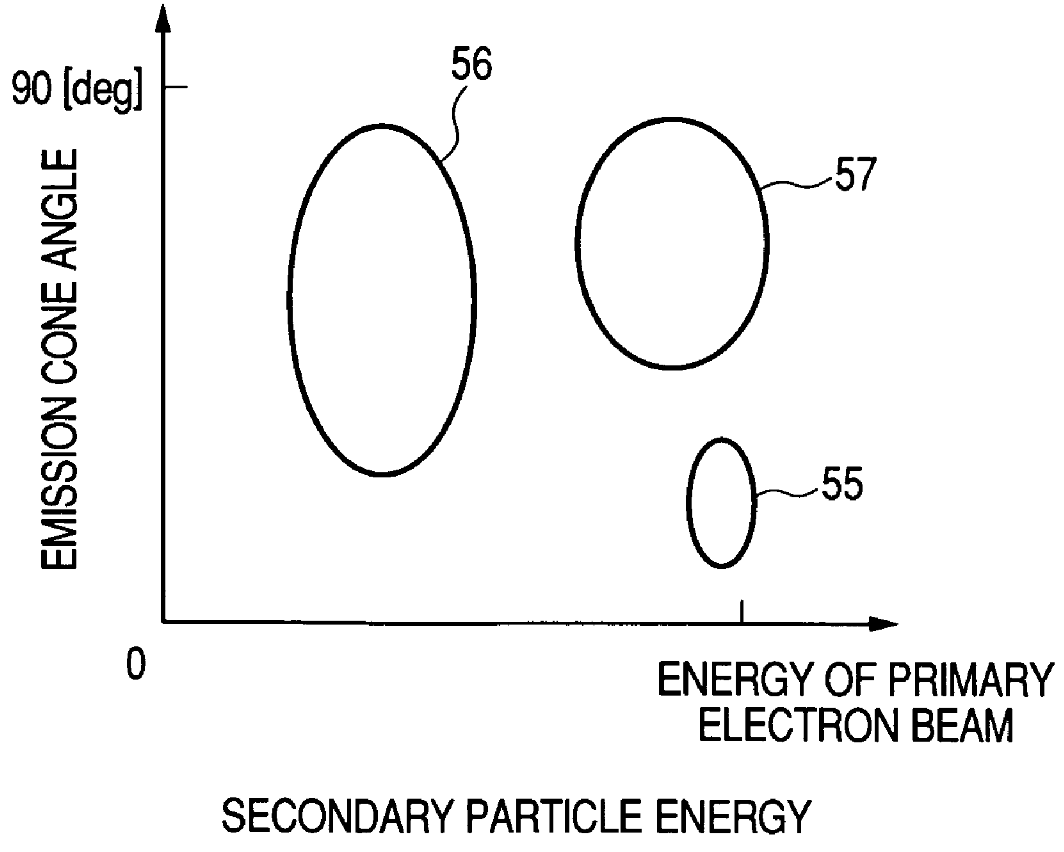
FIG. 13 is a diagram showing a phase map example of an energy which can be detected in the ninth embodiment and an emission cone angle, which is displayed on the interface.

The excitation current of the detection lens 31 can be arbitrarily set by the user. In this situation, the information on the secondary particles which is detected by the respective detection units 52 to 54 is supplied to the user. For that reason, the detectable energy of the secondary electrons and the phase map of the emission cone angle can be displayed on the interface of the image display system 6. FIG. 13 shows an example of the detectable energy and the phase map of the emission cone angle. The phase regions of the secondary particles that are detected by the detection units 52 to 54, respectively, that is, the high-energy small-cone angle reflected electrons 48, the electrons 49 of the intermediate energy to be detected, and the high-energy large-cone angle reflected electrons 50 are indicated by regions 55, 56, and 57, respectively.

The detection units 52 and 54 in this embodiment substantially play the roles performed by the detection system A and the detection system C in the first and second embodiments. Therefore, in this embodiment, the detection system A and the detection system C are not required to be further added. Also, in this embodiment, the installation position of the scanning deflector corresponding to the scanning deflector 11 in the first and second embodiments can be somewhere between the specimen and the C3 lens 23, for example, between the electrode of the detection unit 54 and the detection lens 31, or between the electrode of the detection unit 52 and the C3 lens 23. Further, as the aperture corresponding to the aperture 36 in the second embodiment, an aperture for limiting the secondary particles directed toward the more upstream detection unit can be located upstream of the electrodes of the respective detection units 53 and 54.

What is claimed is:

1. A scanning electron microscope that scans a specimen using an objective lens with a primary electron beam which is emitted from an electron gun to obtain a scan image of the specimen, the scanning electron microscope comprising:

a plurality of circular symmetric magnetic field lenses disposed between the objective lens and the electron gun, one of the circular symmetric magnetic field lenses that is not closest to the objective lens among the plurality of circular symmetric magnetic field lenses forming a crossover point of the primary electron beam in a magnetic field that is formed by the circular symmetric magnetic field lens that is closest to the objective lens among the plurality of circular symmetric magnetic field lenses; and a detection unit to detect secondary particles that are generated from the specimen by irradiation of the primary electron beam, the detection unit being disposed between the circular symmetric magnetic field lens that is closest to the objective lens and the circular symmetric magnetic field lens that forms the crossover point of the primary electron beam.

2. The scanning electron microscope according to claim 1, wherein the detection unit comprises a single or a plurality of detectors.

3. The scanning electron microscope according to claim 1, wherein the detection unit comprises a conversion unit disposed between the plurality of circular symmetric magnetic field lenses and the electron gun which converts the secondary particles into signal electrons; and a detector disposed out of the optical axis which detects the signal electrons.

4. The scanning electron microscope according to claim 1, wherein an aperture for allowing only the secondary particles of a desired energy width to pass through the aperture is disposed between the plurality of circular symmetric magnetic field lenses and the detection unit.

5. A scanning electron microscope wherein the aperture of claim 4 is movable vertically in the primary electron beam direction, and the diameter of the aperture is variable step by step.

* * * * *